(12) United States Patent
Lee et al.

(10) Patent No.: US 8,642,763 B2
(45) Date of Patent: Feb. 4, 2014

(54) NI COMPLEX AND ITS DERIVATIVES, PRODUCING METHOD, AND THE USE THEREOF AS AN ANTIOXIDANT

(75) Inventors: Way-Zen Lee, Taipei (TW); Chien-Wei Chiang, Taipei (TW); Tsung-Han Lin, Taipei (TW); Ting-Shen Kuo, Taipei (TW)

(73) Assignee: National Taiwan Normal University, Taipei (TW)

( * ) Notice: Subject to any disclaimer, the term of this patent is extended or adjusted under 35 U.S.C. 154(b) by 0 days.

(21) Appl. No.: 13/492,657

(22) Filed: Jun. 8, 2012

(65) Prior Publication Data

US 2013/0317224 A1    Nov. 28, 2013

(30) Foreign Application Priority Data

May 22, 2012   (TW) .............................. 101118168 A

(51) Int. Cl.
*C07D 213/89*    (2006.01)
(52) U.S. Cl.
USPC .............................................................. 546/6
(58) Field of Classification Search
CPC .................................................... C07D 213/89
See application file for complete search history.

(56) References Cited

PUBLICATIONS

Reddy, BVS. et al. Asymmetric henry reaction catalyzed by a chiral Cu(II) complex: a facile enantioselective synthesis of (S)-2-nitro-1-arylethanols. Tetrahedron: Asymmetry. 2011, vol. 22, p. 533, figure 2.*
Turkseven, S. et al. Antioxidant mechanism of heme oxygenase-1 involves an increase in superoxide dismutase and catalase in experimental diabetes. An J Physiol Heart Circ Physiol. 2005, vol. 289, p. H701, left column, lines 6-11.*
Frankel, EN. et al. The problems of using one-dimensional methods to evaluate multifunctional food and biological antioxidants. Journal of the Science of Food and Agriculture. 2000, vol. 80, p. 1937, conclusion, line 4.*
Lee et al., "A Discrete Five-Coordinate Ni[III] Complex Resembling the Active Site of the Oxidixed Form of Nickel Superoxide Dismutase," Chemistry: A European Journal, Dec. 9, 2011, pp. 50-53.

* cited by examiner

Primary Examiner — Rita Desai
Assistant Examiner — Ben S Michelson

(74) *Attorney, Agent, or Firm* — Muncy, Geissler, Olds & Lowe, PLLC

(57) ABSTRACT

The present invention relates to a novel nickel complex and its derivatives, which mimic the active site of Ni-containing superoxide dismutase (NiSOD). The five-coordinate Ni(II) and Ni(III) complexes or their derivatives, and six-coordinate derivatives have the following structures of formula (I) and (II):

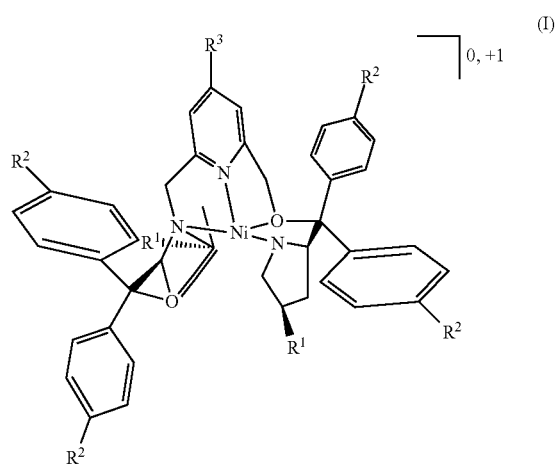

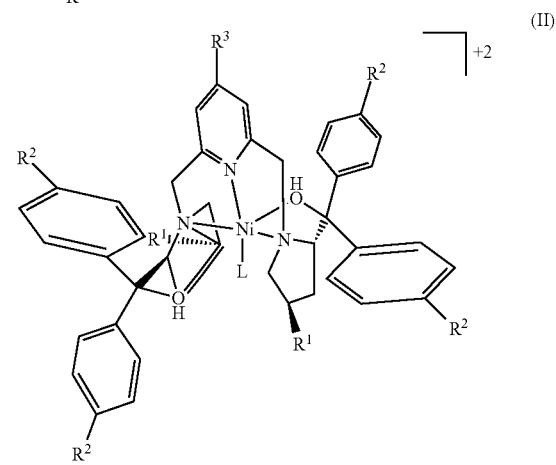

The nickel complexes and their derivatives of the invention act as anti-oxidants or free radical scavengers. The invented nickel complexes can be used in the preparation of medicines, health foods or cosmetics for human, animals and plants, or can be used in environmental or soil protection.

7 Claims, 8 Drawing Sheets

(5 of 8 Drawing Sheet(s) Filed in Color)

Conv. = 52%
T.O.N. = 5.2

Conv. = 72%
T.O.N. = 7.2

NI COMPLEX AND ITS DERIVATIVES, PRODUCING METHOD, AND THE USE THEREOF AS AN ANTIOXIDANT

BACKGROUND OF THE INVENTION

1. Field of the Invention

The present invention relates to a novel Ni complex able to remove free radicals, its derivatives, its producing method, and compositions containing the Ni complex or its derivative. More particularly, the invented Ni complex and its derivatives can mimic the active site of the Ni-containing superoxide dismutase (NiSOD).

2. Description of the Related Art

Free radicals, such as superoxide radical, hydroxyl radical, methyl radical, correlate with senescence and most diseases of human bodies. Free radicals are very active and participate in chain reactions inside cells, overoxidizing the lipid of cellular biomembranes and destroying the structures and functions thereof. Free radicals may also denature or crosslink proteins, disabling enzymes and hormones, and degrading immunity, reflex and mobility of human bodies. Further, free radicals may damage structures of nucleic acids, cause disorders of metabolism, and finally bring about diseases of organisms.

Although free radicals may result in various harms to human bodies, human bodies possess systems to remove or inhibit free radicals. Some of the abovementioned systems are implemented by antioxidative enzymes, which function as antioxidants in the systems. Superoxide dismutases (SODs) are the main antioxidative enzymes, which can eliminate superoxide radicals and thus play an important role in defending against the toxicity of oxygen, decelerating senescence, and preventing from senile diseases.

Superoxide dismutases (SODs) are metalloenzymes and can be categorized into three types: the copper and zinc-containing superoxide dismutase (CuZnSOD), the manganese-containing superoxide dismutase (MnSOD) or the iron-containing superoxide dismutase (FeSOD), and the nickel-containing superoxide dismutase (NiSOD). SODs can catalyze the dismutation of superoxide radicals and convert them into oxygen and hydrogen peroxide.

Recently, it was found that the Ni-containing superoxide dismutase isolated from streptomyces and marine cyanobacteria can catalyze the dismutation of $O_2^-$ into $O_2$ and $H_2O_2$ through a cycle of nickel(II) and nickel(III) oxidation states (H.-D. Youn, et al., Arch. Biochem. Biophys. 1996, 334, 341-348; B. Palenik, et al., Nature 2003, 424, 1037-1042). In these papers, it is reported that the active site of the reduced NiSOD has a nickel(II) ion and the active site of the oxidized NiSOD has a nickel(III) ion. The coordinations of the reduced NiSOD and the oxidized NiSOD are shown as follows:

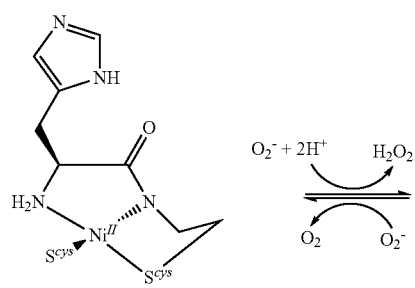

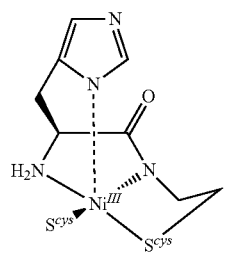

So far have been synthesized several model compounds with a $N_2S_2$ square planar geometry for the active site of NiSOD (J. J. Smee, et al., Inorg. Chem. 2001, 40, 3601-3605). However, only peptide-supported model compounds have been proved to have the NiSOD-like catalytic ability (J. Shearer, L. M. Long, Inorg. Chem. 2006, 45, 2358-2360). No synthetic model has shown the function yet.

SUMMARY OF THE INVENTION

The primary objective of the present invention is to construct a five-coordinate nickel complex, NiBDPP, for mimicking the active site of the nickel-containing superoxide dismutase (NiSOD).

The present invention proposes the five-coordinate nickel complex, NiBDPP, the derivatives thereof, and the six-coordinate derivatives thereof, respectively, having the following structural formulae (I) and (II):

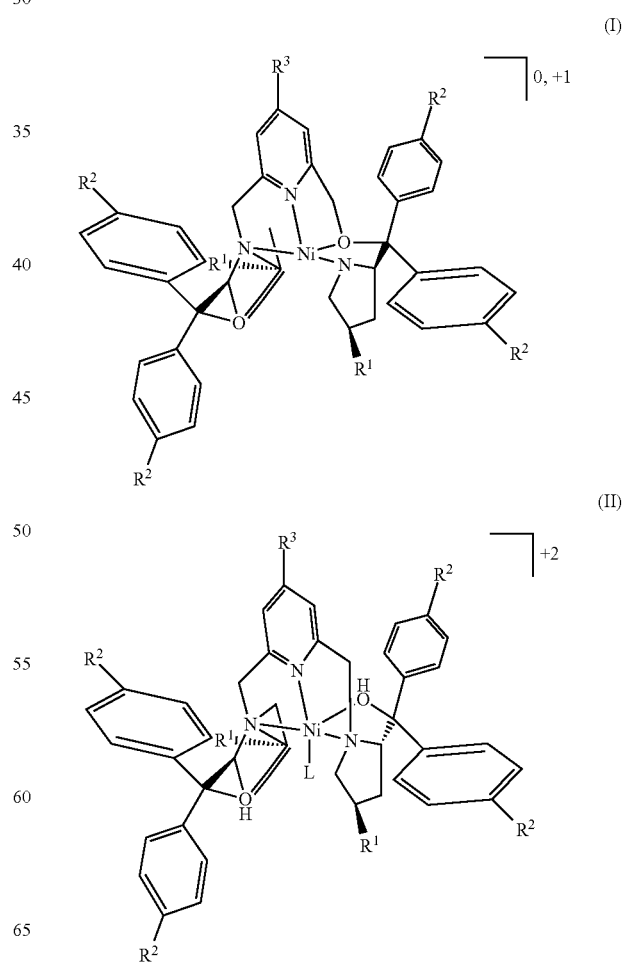

In the abovementioned structural formulae, $R^1$ denotes H or -A-R'; A denotes O or N; R' is H, an alkoxy group, an amino acid group, or a polymeric group, such as a polyethyleneoxy group, a polydimethylsiloxane group, or polyurethane; $R^2$ is a para-substituent of a phenyl ring, which can be selected from a group consisting of alkyl groups, alkoxy groups, silane groups, amino groups, alkyl amino groups, and the hydroxyl group; $R^3$ is a para-substituent of a pyridine ring, which can be selected from a group consisting of amino groups, alkyl amino groups, siloxane amino groups, and siloxane amino groups which attach to a $Fe_3O_4/SiO_2$ magnetic nanoparticle. In the abovementioned structural formulae, the original atom or group can be replaced or not be replaced by the abovementioned substituent; nickel can be a nickel(II) or nickel (III) ion; L can be acetonitrile, water or tert-butyl isocyanate.

In one embodiment, A of the NiBDPP complex adopts O, and R' of the NiBDPP complex adopts H. In another embodiment, A of the NiBDPP complex adopts O, and R' of the NiBDPP complex adopts n pieces of polyethyleneoxy groups, wherein n is an integer of from 1 to 3.

In one embodiment, the phenyl ring of the NiBDPP complex is attached with a $C_{1-6}$ alkoxy group. In another embodiment, the phenyl ring of the NiBDPP complex is attached with a $C_{1-6}$ silane group, wherein the silane group can be replaced or not be replaced by a $C_{1-6}$ alkyl group.

The present invention also proposes a method for producing the five-coordinate nickel complex, NiBDPP, the derivatives thereof, and the six-coordinate derivatives thereof, wherein 2,6-bis(((S)-2-(diphenyl-hydroxymethyl)-1-pyrrolidinyl)methyl)pyridine ($H_2BDPP$) or the derivative thereof is sequentially reacted with NaH and $[Ni(CH_3CN)_6](ClO_4)_2$ to obtain the five-coordinate nickel complex, NiBDPP, and wherein $H_2BDPP$ or the derivative thereof is reacted with $[Ni(CH_3CN)_6](ClO_4)_2$ to obtain the six-coordinate nickel complex, $[NiH_2BDPP(L)](ClO_4)_2$.

In one embodiment, in order to produce a derivative of the five-coordinate nickel complex NiBDPP, the corresponding derivative of $H_2BDPP$ is synthesized firstly; then the derivative of $H_2BDPP$ is reacted with NaH and $[Ni(CH_3CN)_6](ClO_4)_2$ to obtain the derivative of the five-coordinate nickel complex NiBDPP. Whereas, a six-coordinate derivative of NiBDPP was obtained by reacting the derivative of $H_2BDPP$ with $[Ni(CH_3CN)_6](ClO_4)_2$.

The present invention also proposes an antioxidant compound containing the abovementioned five-coordinate nickel complex, NiBDPP, the derivative thereof, or the six-coordinate derivative thereof. The antioxidant compound of the present invention can be used in the preparation of medicines, health foods and cosmetics, and can be used in environmental or soil protection.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
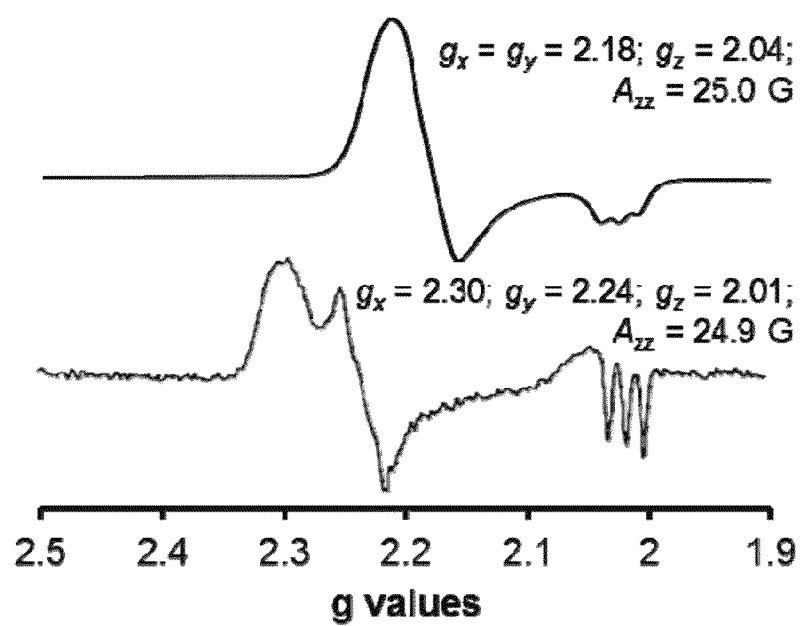
FIG. 1 shows the EPR (Electron Paramagnetic Resonance) spectrum of the five-coordinate nickel(III) complex, [NiBDPP]$PF_6$, according to one embodiment of the present invention, wherein the lower curve is the reference spectrum of an oxidized NiSOD isolated from streptomyces.

The present invention proposes a five-coordinate nickel complex, NiBDPP, the derivatives thereof, and the six-coordinate derivatives thereof, respectively, having the following structural formulae (I) and (II):

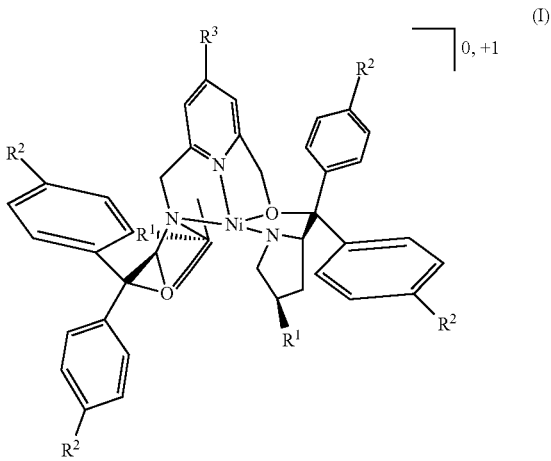

-continued

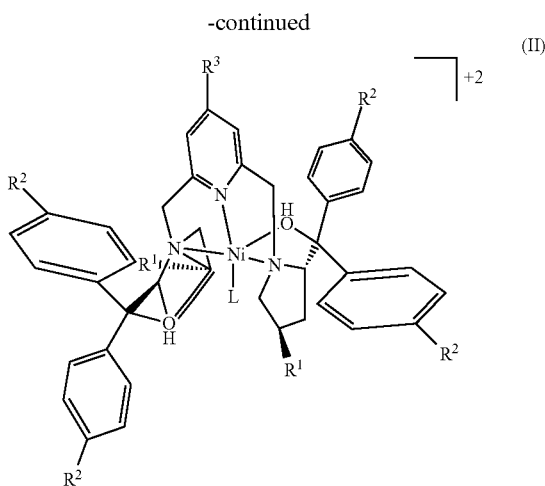

(II)

In the abovementioned structural formulae, $R^1$ denotes H or -A-R'; A denotes O or N; R' is H, an alkoxy group, an amino acid group, or a polymeric group, such as a polyethyleneoxy group, a polydimethylsiloxane group, or polyurethane; $R^2$ is a para-substituent of a phenyl ring, which can be selected from a group consisting of alkyl groups, alkoxy groups, silane groups, amino groups, alkyl amino groups, and the hydroxyl group; $R^3$ is a para-substituent of a pyridine ring, which can be selected from a group consisting of amino groups, alkyl amino groups, siloxane amino groups, and siloxane amino groups which attach to a $Fe_3O_4/SiO_2$ magnetic nanoparticle.

In the abovementioned structural formulae, the original atom or group can be replaced or not be replaced by the abovementioned substituent; nickel can be a nickel(II) or nickel(III) ion; L can be acetonitrile, water or tert-butyl isocyanate.

Except otherwise defined, in the substituent groups, the term "alkyl group" is referred to a non-cyclic monovalent free radical containing a linear chain or branch chains having 1-6 carbon atoms, such as the methyl group, the ethyl group, the propyl group, the n-butyl group, the isopropyl group, the isobutyl group, the 1,1-dimethylethyl group, the 2-methylbutyl group, the n-pentyl group, the dimethylpropyl group, the n-hexyl group, the 2-methylpentyl group, and the 3-methylpentyl group. If the alkyl group has sufficient carbon atoms, i.e. at least three carbon atoms, the alkyl group may be in form of branch chains or a cycle, such as a $C_{3-6}$ cyclic alkyl group. If the alkyl group has sufficient carbon atoms, i.e. at least four carbon atoms, the alkyl group may be in a partially cyclic form or a non-cyclic form. Except otherwise defined, the abovementioned alkyl group may be in a saturated state. If the alkyl group has sufficient carbon atoms, i.e. at least two carbon atoms, the alkyl group is in an unsaturated state except otherwise defined, for example, in form of a $C_{2-6}$ alkenyl group or a $C_{2-6}$ alkynyl group.

The term "alkoxy group" is referred to a substituent wherein one carbon atom of an alkyl free radical is bonded to a nearby oxygen atom. The alkoxy group may be but is not limited to be the methoxy group, the ethoxy group, the propoxy group, the butoxy group, the pentyloxy group, the isopropoxy group, the isobutoxy group, the 3-methylpropoxy group, the isopentyloxy group, or one of the isomers thereof.

The term "polydimethylsiloxane group" is referred to a polymer wherein carbon atoms of an alkyl free radical are replaced by silicon atoms, and wherein an oxygen atom is bonded to two of the silicon atoms.

The term "polyurethane" is referred to a polymer whose backbone contains the urethane-like units.

The term "amino acid group" is referred to one of the natural amino acids or a peptide formed via synthesizing the natural amino acids. The amino acid group may be but is not limited to be glycine, alanine, valine, leucine, isoleucine, phenylalanine, tryptophan, tyrosine, aspartic acid, histidine, asparagine, glutamic acid, lysine, glutamine, methionine, arginine, serine, threonine, cysteine, proline, or a peptide synthesized therefrom.

The term "silane group" is referred to a compound wherein a carbon atom of an alkyl group is replaced by a silicon atom. The silane group may be but is not limited to be the methylsilane group, the ethylsilane group, the dimethylsilane group, the trimethylsilane group, or one of the isomers thereof.

The term "alkyl amino group" is referred to a substituent wherein one or two carbon atoms of an alkyl free radical are bound to nitrogen atoms by single bonds. The alkyl amino group may be but is not limited to be the methylamino group, the dimethylamino group, the ethylamino group, the diethylamino group, the propylamino group, the dipropylamino group, the butylamino group, the dibutylamino group, the isopropylamino group, the diisopropylamino group, the isobutylamino group, the diisobutylamino group, the 3-methylpropylamino group, the di-3-methylpropylamino group, or one of the isomers thereof.

The term "siloxane amino group" is referred to a substituent wherein nitrogen atoms are bound to a nearby siloxane molecule with single bonds and through one or several carbon atoms of an alkyl free radical. The siloxane amino group may be but is not limited to be the 3-(triethoxysilyl)methyl-1-amino group, the 3-(triethoxysilyl)ethyl-1-amino group, the 3-(triethoxysilyl)propyl-1-amino group, or one of the isomers thereof.

The term "magnetic nanoparticle of $Fe_3O_4/SiO_2$" is referred to a magnetic nanoparticle enveloped by $SiO_2$.

The five-coordinate nickel(II) complex, NiBDPP, and the derivatives thereof can be produced via sequentially reacting 2,6-bis(((S)-2-(diphenylhydroxymethyl)-1-pyrrolidinyl)methyl)pyridine ($H_2$BDPP) or the derivative thereof with NaH and $[Ni(CH_3CN)_6](ClO_4)_2$. The nickel(III) complex, [NiBDPP]$PF_6$, can be produced via reacting the nickel(II) complex, NiBDPP, with an equivalent of $[Cp_2Fe]PF_6$. The six-coordinate derivative can be produced via reacting $H_2$BDPP or the derivative of $H_2$BDPP with $[Ni(CH_3CN)_6](ClO_4)_2$.

According to the substituents of the desired derivatives of the five or six-coordinate nickel complex, the corresponding $H_2$BDPP derivatives are synthesized in various ways to obtain the precursors of the desired five or six-coordinate nickel complex. For example, in producing the derivative of the five-coordinate nickel(II) complex, wherein phenyl ring is attached with a methoxy group, firstly synthesize a derivative of BDPP, 2,6-bis(((S)-2-(dimethoxyphenylhydroxymethyl)-1-pyrrolidinyl)methyl)-pyridine (BDPP$^{OMe}$), wherein the phenyl ring is attached with a methoxy group, according to the following steps:

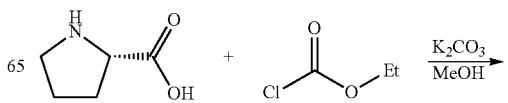

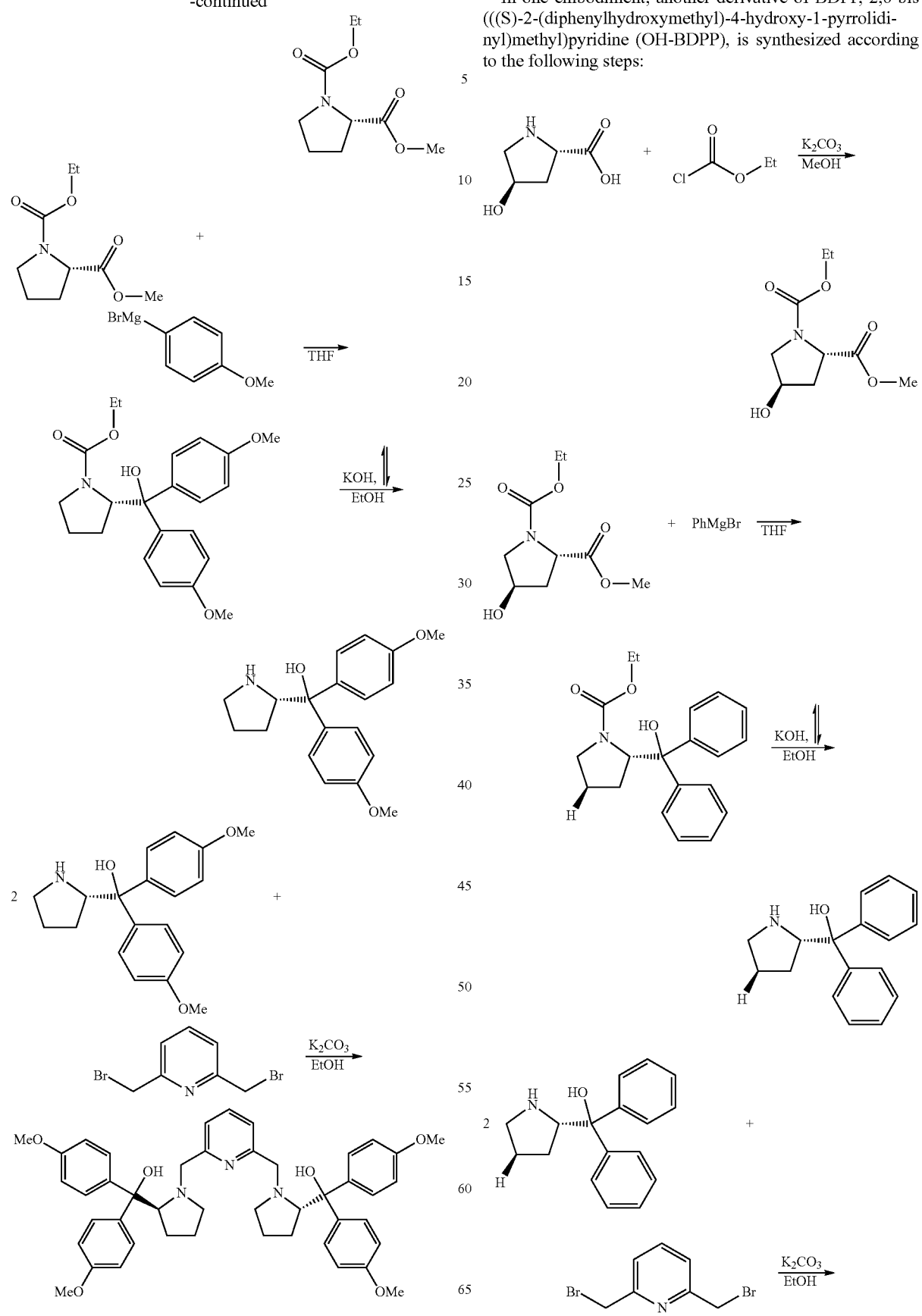
In one embodiment, another derivative of BDPP, 2,6-bis(((S)-2-(diphenylhydroxymethyl)-4-hydroxy-1-pyrrolidinyl)methyl)pyridine (OH-BDPP), is synthesized according to the following steps:

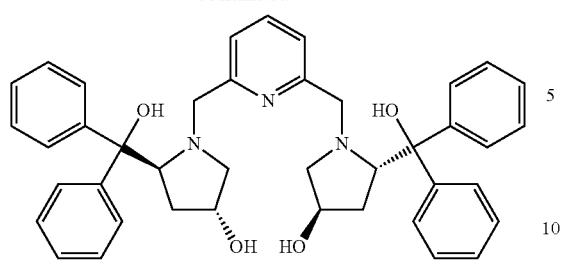

In one embodiment, yet another derivative of BDPP, 2,6-bis(((S)-2-(diphenylhydroxymethyl)-4-triethoxy-1-pyrrolidinyl)methyl)pyridine (OTEG-BDPP), is synthesized according to the following steps:

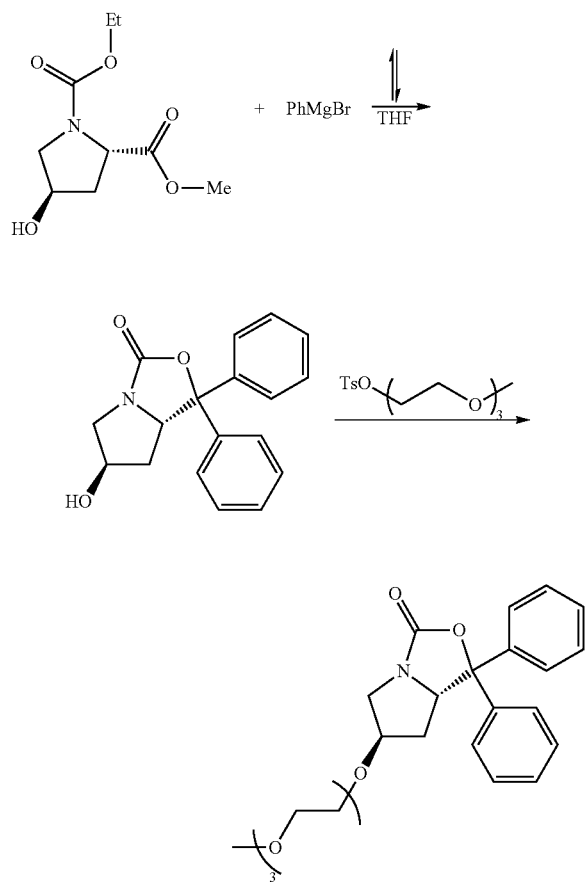

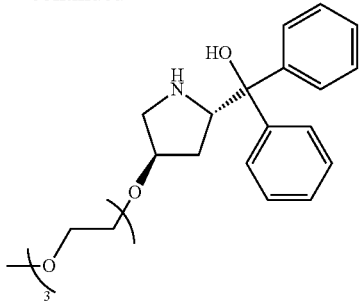

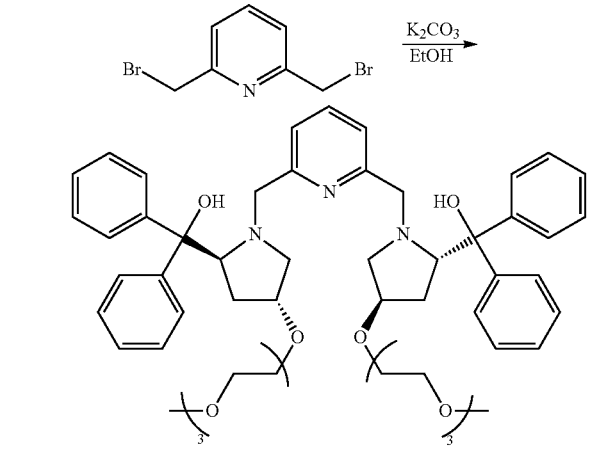

According to requirement, the persons skilled in the art may modify the nickel complex and its derivatives of the present invention, or modify the precursors of BDPP to synthesize the corresponding derivatives of the nickel complex. In some embodiments, hydrophilic or lipophilic groups are bound to the phenyl ring or pyrrolidine ring of the nickel complex to regulate the solubility of the nickel complex in water or another solvent, so that the present invention can apply to various fields. The following table lists the solubility of the nickel complex and its derivatives in water and other solvents.

| Sample | Solubility |
|---|---|
| NiBDPP | dissolvable in $CH_2Cl_2$, THF; undissolvable in MeOH |
| NiBDPP$^{OMe}$ | dissolvable in $CH_2Cl_2$, THF; undissolvable in MeOH; 1.0 mg complex dissolvable in 250 μL DMSO/1 mL $H_2O$ |
| NiH$_2$BDPP($^t$BuNC) | 1.0 mg complex dissolvable in 150 μL MeOH/1 mL $H_2O$ |
| Ni-OH-BDPP | 1.5 mg complex dissolvable in 40 μL MeOH 1.5 mg complex dissolvable in |

-continued

| Sample | Solubility |
|---|---|
| Ni-OH-BDPP$^{TMS}$ | 250 μL MeOH/1 mL H$_2$O 1.0 mg complex dissolvable in 270 μL EtOH/1 mL H$_2$O 1.0 mg complex dissolvable in 750 μL MeOH/1 mL H$_2$O |
| Ni-OTEG-BDPP | 1.0 mg complex dissolvable in 100 μL EtOH/1 mL H$_2$O |

It has been known that superoxide dismutase (SOD) can specifically eliminate harmful free radicals. Therefore, SOD can prevent free radicals from oxidizing some constituents of organisms and exempt organism from harms, such as oxygen poisoning, acute inflammations, edemas, autoimmune diseases, and radiation diseases, which all correlate with toxicity of reactive oxygen. The clinical trial of SOD proves that SOD can prevent can treat cardiovascular and cerebrovascular diseases. SOD can regulate blood lipid and thus can prevent from atherosclerosis and hyperlipidemia-induced cardio/cerebrovascular diseases. SOD can further delay free radical-induced senescence and senile dementia. The five-coordinate nickel complex of the present invention has activity similar to that the active side of NiSOD and can dismutate superoxide radicals into oxygen and hydrogen peroxide. Therefore, the five-coordinate nickel complex of the present invention can be used to fabricate antioxidant medicines.

The five-coordinate nickel complex, the derivatives thereof and the six-coordinate derivatives thereof can be fabricated into any dosage form known in the field of medicine, including the dosage forms for regional or universal delivery. While not intended to be absorbed by the intestine track, the medicine of the present invention is preferred to inject into the body via intramuscular injection, intravenous injection, intraperitoneal injection, or hypodermic injection. The medicine of the present invention can also be delivered orally in form of powder, tablets or capsules. When delivered into an organism, the five- or six-coordinate nickel complex or its derivative can effectively capture free radicals and prevent free radical from damaging proteins. When intended to be injected into an organism, the medicine of the present invention is fabricated into a liquid solution. It is preferable to dissolve the medicine of the present invention in a physiologically acceptable buffer solution, such as the Hank's solution or the Ringer's solution. The medicine of the present invention can also be fabricated into a solid state via such as a freeze-drying way. The solid-state medicine is dissolved or suspended in liquid the moment that it is to be used.

The solid-state product of the present invention, together with medically acceptable excipients, can be fabricated into oral medicine in form of tablets, lozenges or capsules with a conventional method. The medically acceptable excipients include binders (such as gelatinized corn starch, polyvinylene-pyrrolidone, and hydroxypropyl methyl cellulose (HPMC)); fillers (such as lactose, microcrystalline cellulose, and calcium hydrogenphosphate); lubricants (such as magnesium stearate, talc, and silica); disintegration agents (such as potato starch, and sodium starch glycolate); and wetting agents (such as sodium lauryl sulfate). The tablets or lozenges can be further encapsulated with a conventional method.

The product of the present invention can be fabricated into oral medicine in form of solution, syrup, and suspension. Alternatively, the product of the present invention can be fabricated into a dried compound that can be mixed with water or another vehicle the moment it is to be used. The product of the present invention, together with medically acceptable additives, can be fabricated into liquid-state dosage forms with a conventional method. The medically acceptable additives include suspending agents (such as sorbitol syrup, cellulose derivatives, edible hydrogenated fat); emulsifiers (such as lecithin and Cassie oil); non-aqueous vehicles (such as ationd oil); and preservatives (such as methylparaben, propylparaben, and sorbic acid). Buffer salts, flavors, colorants, and sweeteners may also be appropriately added to the liquid-state medicine. Further, the oral-delivery medicine may be appropriately modified to control the releasing rate of the active constituent.

The five- or six-coordinate nickel complex and its derivative of the present invention can also be fabricated into health foods and cosmetics. Owing to aging and some external factors, the skin tissue would generate free radicals whose amount exceeds the scavenging capability of the human body and thus damages the skin tissue. The five- or six-coordinate nickel complex and its derivative of the present invention can be added to foods or beverages, such as mayonnaise, milk, coffee and fruit juices, to enhance the healthcare function thereof.

SOD has been widely used in cosmetics. SOD can inhibit the intense oxidizing action of free radicals on the surface of skin. The five- or six-coordinate nickel complex and its derivative of the present invention can be added to cosmetics, such as masks, balsams, and loose powders.

Besides, the five- or six-coordinate nickel complex and its derivative of the present invention can be added to plant culture soil, environment protection agents, and surface coating agents to function as an antioxidant agent of soil or the environment.

EMBODIMENTS

Embodiments will be used to demonstrate the characteristics and advantages of the present invention. However, it should be understood that these embodiments are only to exemplify the present invention but not to limit the scope of the present invention.

Embodiment I 13  14
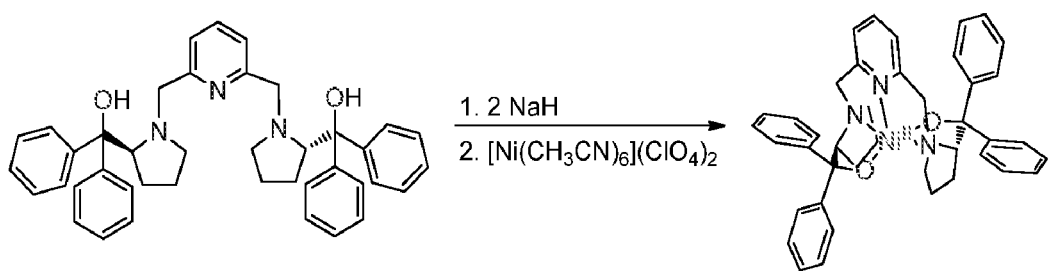
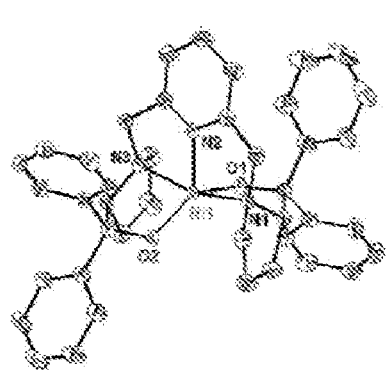
1
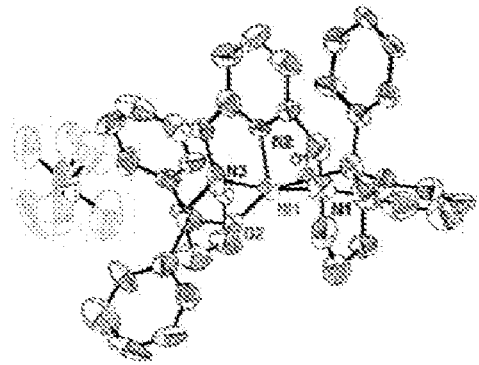
2

Let 0.122 g (0.2 mmol) 2,6-bis(((S)-2-(diphenylhydroxymethyl)-1-pyrrolidinyl)methyl)pyridine (H$_2$BDPP) react with 0.012 g (0.5 mmol) sodium hydride (NaH) in about 10 mL tetrahydrofuran at ambient temperature for one hour to obtain deprotonated BDPP$^{2-}$. Next, let BDPP$^{2-}$ react with 0.101 g (0.2 mmol) [Ni(CH$_3$CN)$_6$](ClO$_4$)$_2$ in 15 mL dry acetonitrile at ambient temperature for 2 hours to obtain the green five-coordinate nickel(II) complex, NiBDPP, with a yield of 63% (0.017 g). The nickel(II) complex, NiBDPP, has a characteristic absorption band at 350 nm ($\epsilon$=830 M$^{-1}$cm$^{-1}$) in the UV/Vis spectrum and two transition bands at 690 and 1080 nm (c=20 and 30 M$^{-1}$cm$^{-1}$), respectively. The element analysis result for C$_{41}$H$_{41}$N$_3$O$_2$Ni is [C, 73.89; H, 6.20; N, 6.30] theoretically, and [C, 73.55; H, 6.26; N, 6.24] in practice.

Dissolve 0.133 g (0.2 mmol) NiBDPP in methylene dichloride. Next, use 1 eq of [Cp$_2$Fe]PF$_6$ (0.066 g, 0.2 mmol) to oxidize NiBDPP in an ice bath for 1 hour to form the five-coordinate nickel(III) complex, [NiBDPP]PF$_6$, with a yield of 70% (0.133 g). [NiBDPP]PF$_6$ has three CT bands at 300, 380 and 450 nm (c=4950, 4650 and 2550 M$^{-1}$cm$^{-1}$), respectively. Reddish-brown crystals of [NiBDPP]PF$_6$ are obtained via a slow diffusion method over two days. The X-ray analysis reveals that the structure of the nickel(III) complex, [NiBDPP]PF$_6$, possesses a five-coordinate geometry with a $\tau$ value of 0.24, which is very close to that of the active site of the oxidized NiSOD ($\tau$=0.20), indicating that the center of the five-coordinate nickel(III) complex, [NiBDPP]PF$_6$, has a square pyramidal ligand environment. FIG. 1 shows that the 77 K X-band EPR (Electron Paramagnetic Resonance) of [NiBDPP]PF$_6$ has an axial signal ($g_x$=$g_y$=2.18 and $g_z$=2.04) with a superhyperfine triplet ($A_{zz}$=25.0 G), which is similar to the splitting pattern of the oxidized NiSOD isolated from streptomyces.

Figure 2:
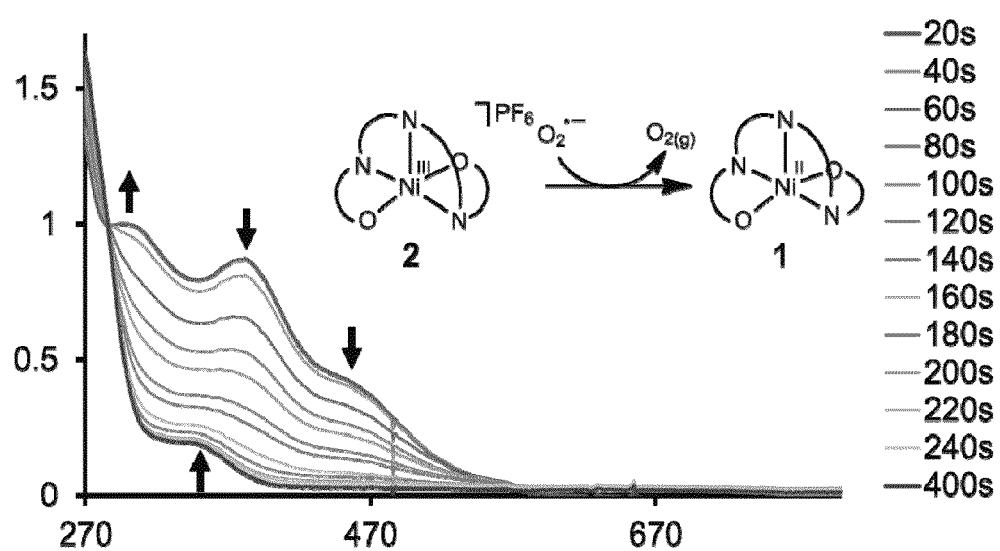
FIG. 2 shows the results of the UV/Vis spectroscopic analysis of the products generated by the reaction of $KO_2$ and the five-coordinate nickel(III) complex, [NiBDPP]$PF_6$, in $CH_3CN$ according to one embodiment of the present invention.

In order to test whether the five-coordinate nickel(III) complex, [NiBDPP]PF$_6$, can work similarly to SOD that can convert O$_2^-$ into O$_2$, let [NiBDPP]PF$_6$ (0.04 mmol) reacts with excess KO$_2$ in dry acetonitrile at 30° C. The reason why excess KO$_2$ is used is that KO$_2$ is hard to dissolve in dry acetonitrile. Within 3 minutes, the reaction solution rapidly turns from brown to green and generates an equivalent of O$_2$. In FIG. 2, the UV/Vis spectroscopic analysis shows that two isosbestic points are observed at 285 and 570 nm, respectively, while sequential spectra were collected, indicating that the nickel(III) complex, [NiBDPP]PF$_6$, is directly converted into the nickel(II) complex, NiBDPP, while O$_2^-$ is converted into O$_2$. Via GC analysis, the amount of O$_2$ generated by the abovementioned reaction is estimated to be 0.96 mL. In comparison with other neutral square planar nickel(II) complexes, the five-coordinate nickel(II) complex, NiBDPP, supported by a pentadentate BDPP$^{2-}$ ligand of the present invention has a lower redox potential and is more likely to be oxidized into the nickel(III) complex that can convert radical O$_2^-$ into O$_2$. Furthermore, the nickel(III) complex can be directly reduced into the nickel(II) complex forming a cycle of oxidation state transition of nickel(II) and nickel(III).

Add 0.122 g (0.2 mmol) H$_2$BDPP and 0.068 g (0.2 mmol) Ni(BF$_4$)$_2$.6H$_2$O to 15 mL dry acetonitrile, and heat the mixture to 50° C. to dissolve the solids. During the process, the solution turns from blue to violet. After the abovementioned reaction has been undertaken for 1 hour, add 22.6 µL (0.082 mmol) tert-butyl isocyanide to the reaction solution, and continue to undertake the reaction for 1 hour to obtain the violet six-coordinate nickel(II) complex, [NiH$_2$BDPP($^t$BuNC)](BF$_4$)$_2$, with a yield of 63% (0.082 g). The X-ray single crystal diffraction shows that [NiH$_2$BDPP($^t$BuNC)](BF$_4$)$_2$ has the following structure:

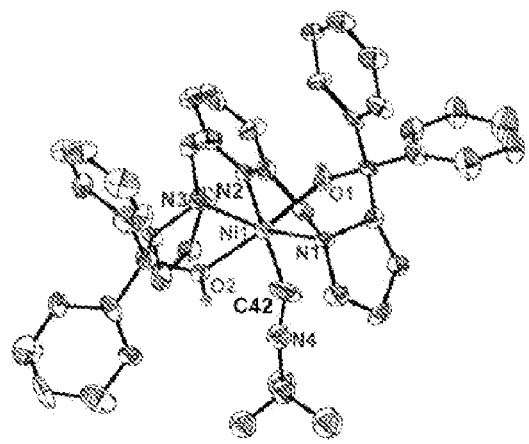

Figure 3:
FIG. 3 shows the results of peroxide test paper tests of the reaction of $KO_2$ and the six-coordinate nickel(II) complex, [NiH$_2$BDPP-($^t$BuNC)]($BF_4$)$_2$, according to one embodiment of the present invention, wherein the right test paper shows test result recorded as the reaction has proceeded for 5 seconds, and wherein the middle test paper shows the test result recorded as the reaction has proceeded for 20 seconds, and wherein the left test paper shows the test result recorded as the reaction has proceeded for 1 minute. The fact that blue color appears on the test paper indicates that $H_2O_2$ has been generated. As the reaction has proceeded for 20 seconds to 1 minute, the color faded out gradually because $H_2O_2$ reacted with a Ni complex existed in the reaction solution and was decomposed.

In order to test whether the proton-containing six-coordinate nickel(II) complex, [NiH$_2$BDPP($^t$BuNC)](BF$_4$)$_2$, can work similarly to SOD, that can convert superoxide radical (O$_2^-$) into hydrogen peroxide (H$_2$O$_2$), test paper of hydrogen peroxide (purchased from Merck Chemical Co.) is employed to test the reaction product of KO$_2$ and the proton-containing six-coordinate nickel(II) complex, [NiH$_2$BDPP($^t$BuNC)](BF$_4$)$_2$, of the present invention. As seen in FIG. 3, blue color appears on the test paper after the test reaction has been undertaken for 5 seconds, indicating that H$_2$O$_2$ has been generated. After the reaction has proceeded for 20 seconds to 1 minute, the color fades out gradually because H$_2$O$_2$ reacts with a catalyst existed in the reaction solution to form O$_2$.

Embodiment II

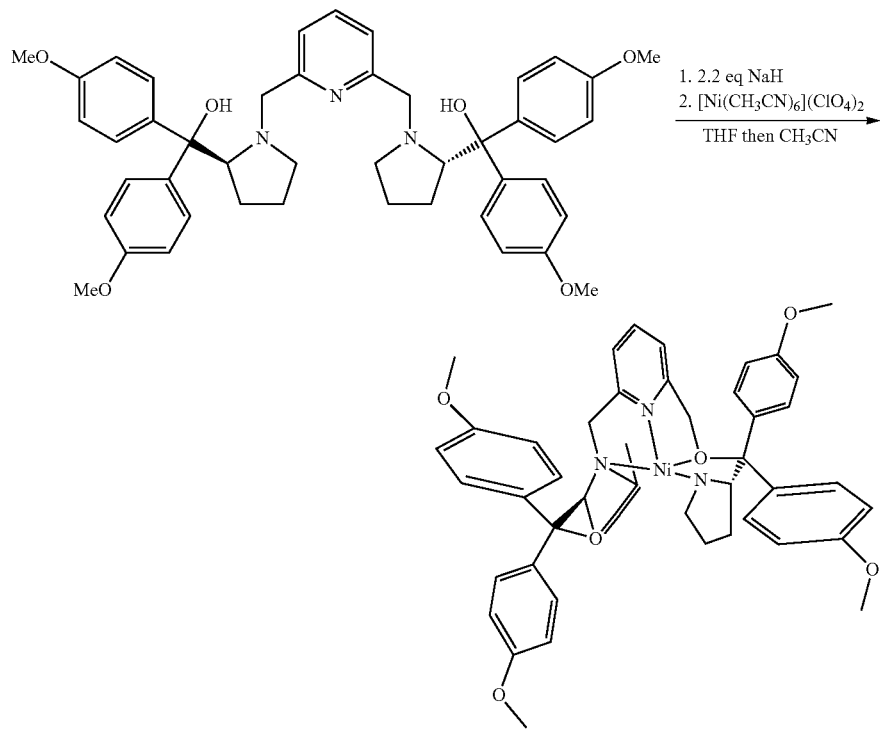

This embodiment adopts a reaction precursor BDPP$^{OMe}$ wherein the phenyl ring of BDPP is attached with a methoxy group. Similarly to Embodiment I, let 0.146 g (0.2 mmol) BDPP$^{OMe}$ sequentially react with 0.012 g (0.5 mmol) NaH and 0.101 g (0.2 mmol) [Ni(CH$_3$CN)$_6$](ClO$_4$)$_2$ at ambient temperature for 2 hours to obtain the five-coordinate nickel (II) complex, NiBDPP$^{OMe}$, with a yield of 50% (0.0853 g). The X-ray single crystal diffraction shows that the five-coordinate nickel(II) complex, NiBDPP$^{OMe}$, has the following structure:

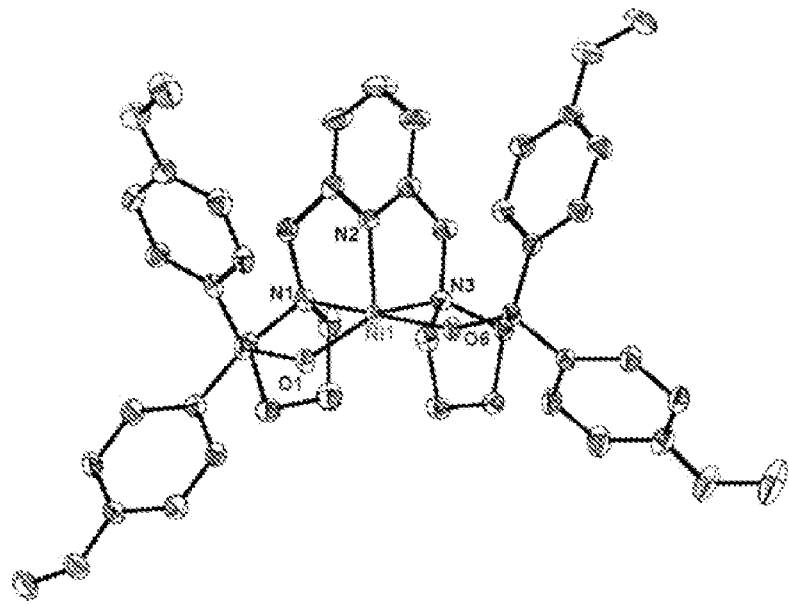

Embodiment III

This embodiment adopts a reaction precursor BDPP$^{TMS}$ wherein the phenyl ring of BDPP is attached with a trimethylsilyl group. Similarly to Embodiment I, let 0.180 g (0.2 mmol) BDPP$^{TMS}$ sequentially react with 0.012 g (0.5 mmol) NaH and 0.101 g (0.2 mmol) [Ni(CH$_3$CN)$_6$](ClO$_4$)$_2$ at ambient temperature for 2 hours to obtain the five-coordinate nickel(II) complex, NiBDPP$^{TMS}$, with a yield of 60% (0.114 g).

Figure 4:
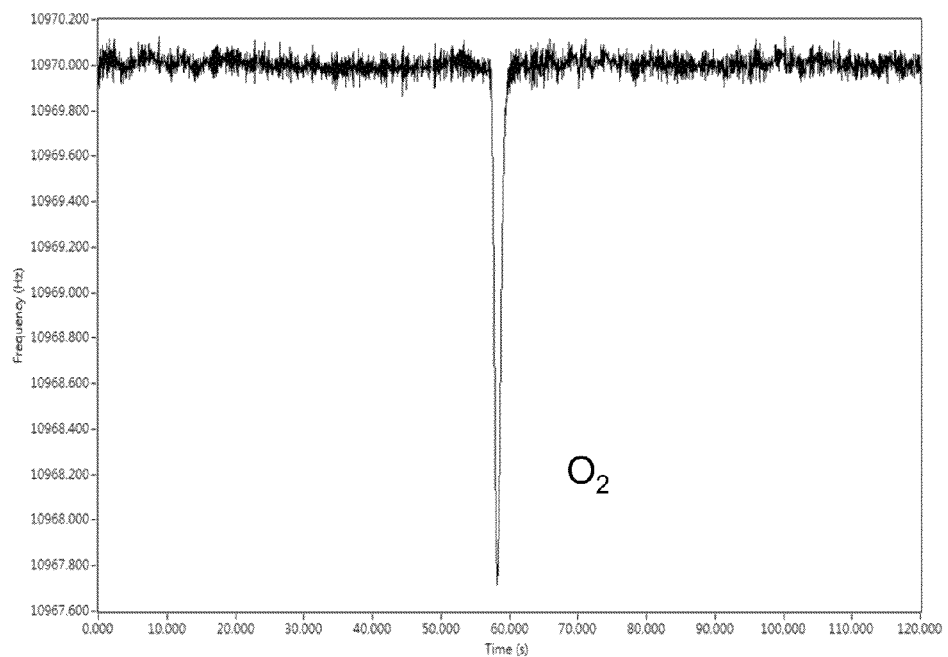
FIG. 4 shows the result of the antioxidant activity analysis of the reaction of $H_2O_2$ and the derivative of the five-coordinate nickel(II) complex, NiBDPP$^{TMS}$, wherein the phenyl ring of BDPP is attached with a trimethylsilyl group. An obvious band of $O_2$ appears in FIG. 4.

The analysis result of the antioxidant activity of the nickel (II) complex, NiBDPP$^{TMS}$, is shown in FIG. 4, indicating that the nickel(II) complex, NiBDPP$^{TMS}$, can work similarly to peroxidase and catalyze H$_2$O$_2$ into O$_2$.

Embodiment IV

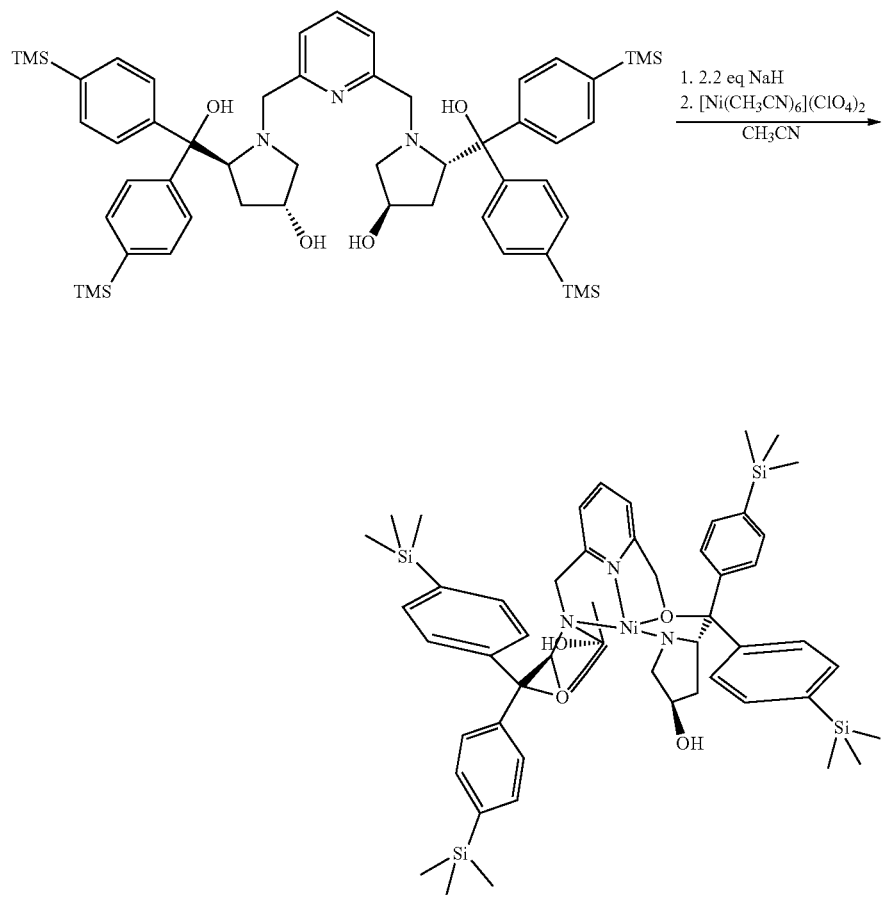

This embodiment adopts a reaction precursor OH-BDPP$^{TMS}$ wherein the phenyl ring of BDPP is attached with a trimethylsilyl group and the pyrrolidinyl group is attached with a hydroxyl group. Similarly to Embodiment I, let 0.186 g (0.2 mmol) OH-BDPP$^{TMS}$ sequentially react with 0.012 g (0.5 mmol) NaH and 0.101 g (0.2 mmol) [Ni(CH$_3$CN)$_6$](ClO$_4$)$_2$ at ambient temperature for 2 hours to obtain a derivative of the five-coordinate nickel(II) complex, Ni—OH-BDPP$^{TMS}$.

Figure 5:
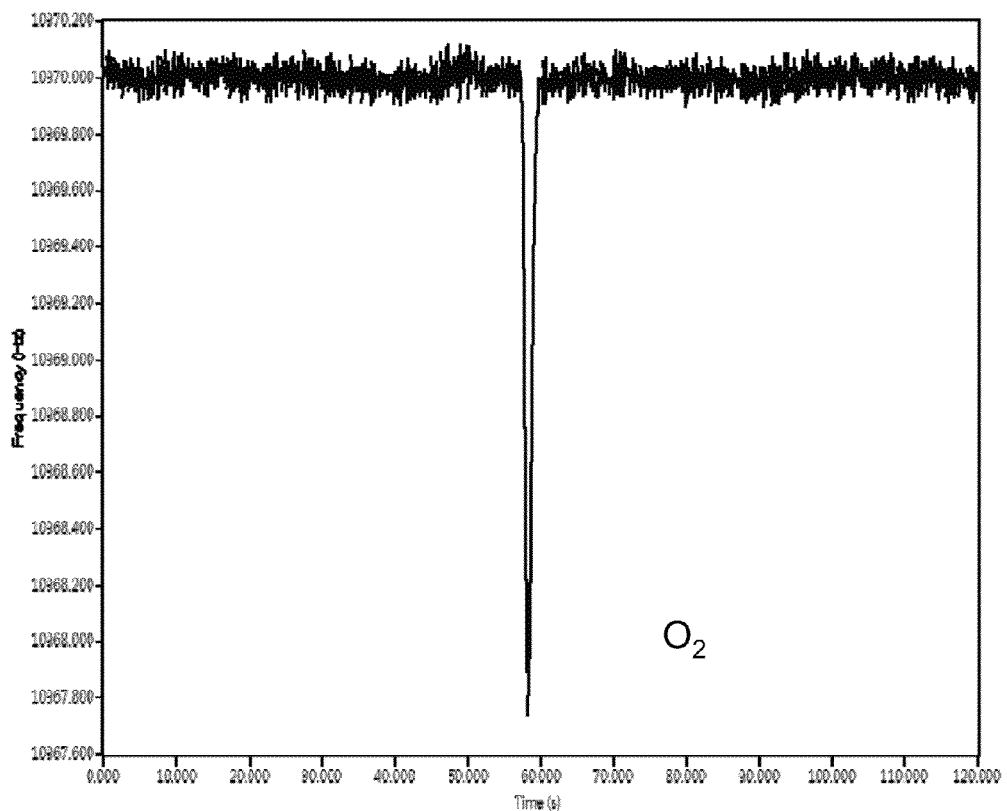
FIG. 5 shows the result of the antioxidant activity analysis of the reaction of $H_2O_2$ and the derivative of the five-coordinate nickel(II) complex, Ni—OH-BDPP$^{TMS}$, wherein the phenyl ring of BDPP is attached with a trimethylsilyl group and the pyrrolidinyl group is attached with a hydroxyl group. An obvious band of $O_2$ appears in FIG. 5.

The analysis result of the antioxidant activity of the nickel (II) complex, Ni—OH-BDPP$^{TMS}$, is shown in FIG. 5, indicating that the nickel(II) complex, Ni—OH-BDPP$^{TMS}$, can work similarly to peroxidase and catalyze H$_2$O$_2$ into O$_2$.

Embodiment V

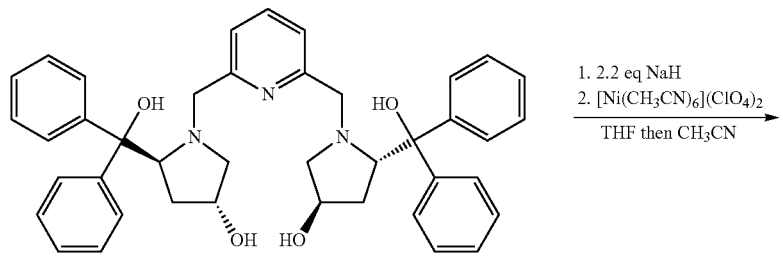

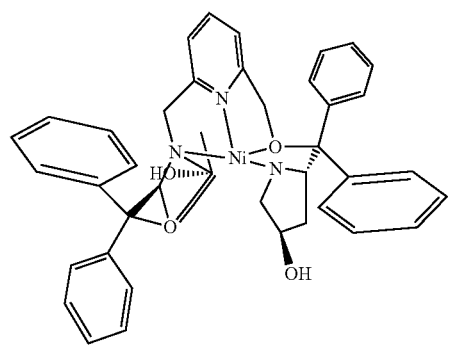

This embodiment adopts a reaction precursor OH-BDPP wherein the pyrrolidinyl group is attached with a hydroxyl group. Similarly to Embodiment I, let 0.128 g (0.2 mmol) OH-BDPP sequentially react with 0.012 g (0.5 mmol) NaH and 0.101 g (0.2 mmol) [Ni(CH$_3$CN)$_6$](ClO$_4$)$_2$ at ambient temperature for 2 hours to obtain a five-coordinate nickel(II) complex, Ni—OH-BDPP.

Two derivatives, a five-coordinate nickel(III) complex, [Ni—OH-BDPP]PF$_6$ (WCt005), and a six-coordinate nickel (II) complex, Ni—OH—H$_2$BDPP (WCt006), were obtained from further fabrication of the abovementioned five-coordinate nickel(II) complex, Ni—OH-BDPP.

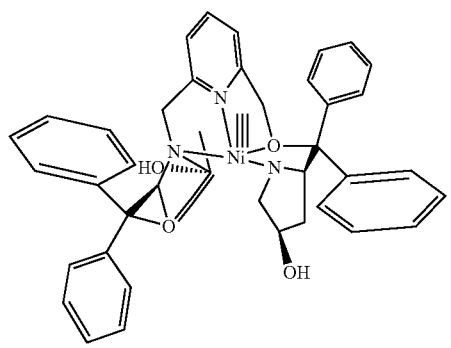

(WCt005)

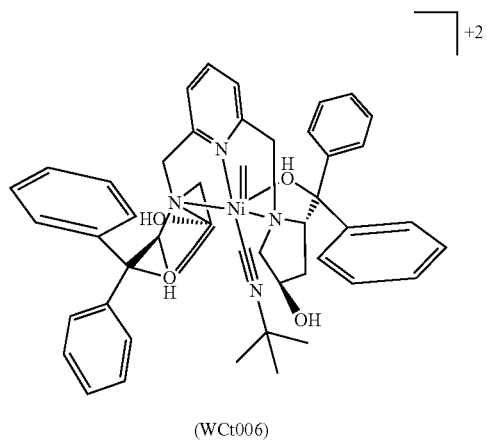

(WCt006)

Figure 6:
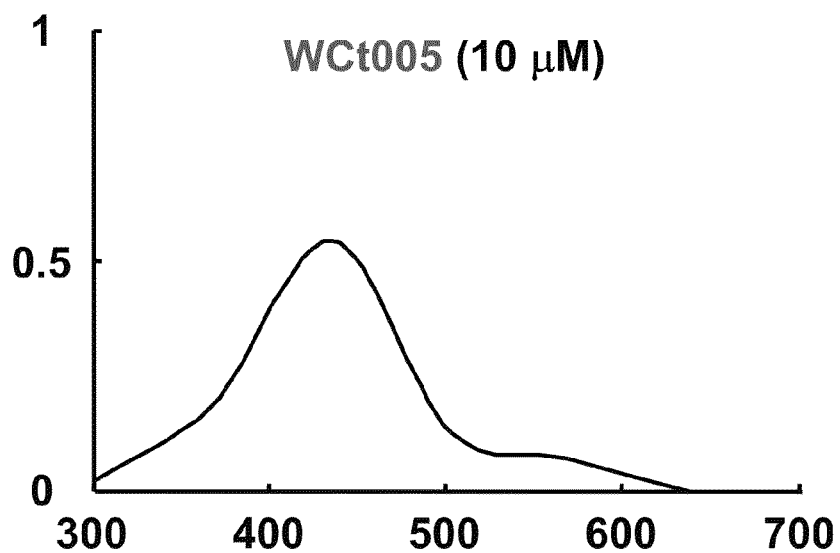
FIG. 6 shows the test results of the SOD-like activity of the five-coordinate nickel complex derivative, [Ni—OH-BDPP]$PF_6$ (WCt005), by the WST SOD assay kit. The lower drawing shows the test results of a blank control group.
Figure 6:
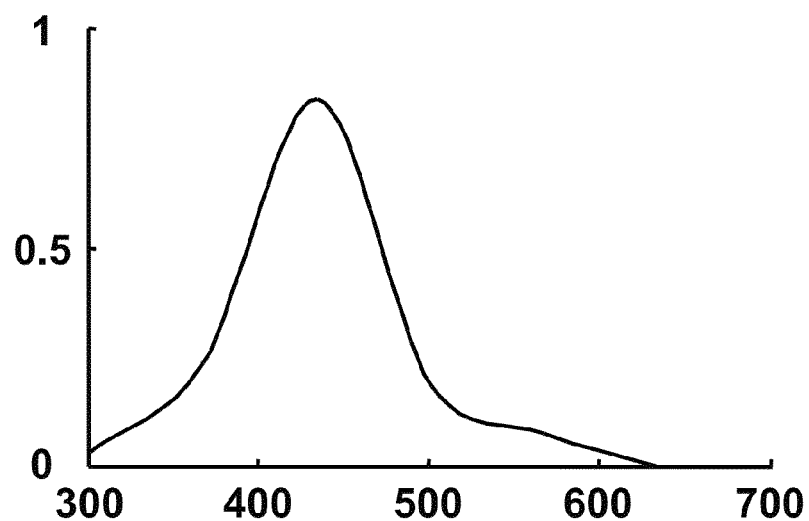
Figure 7:
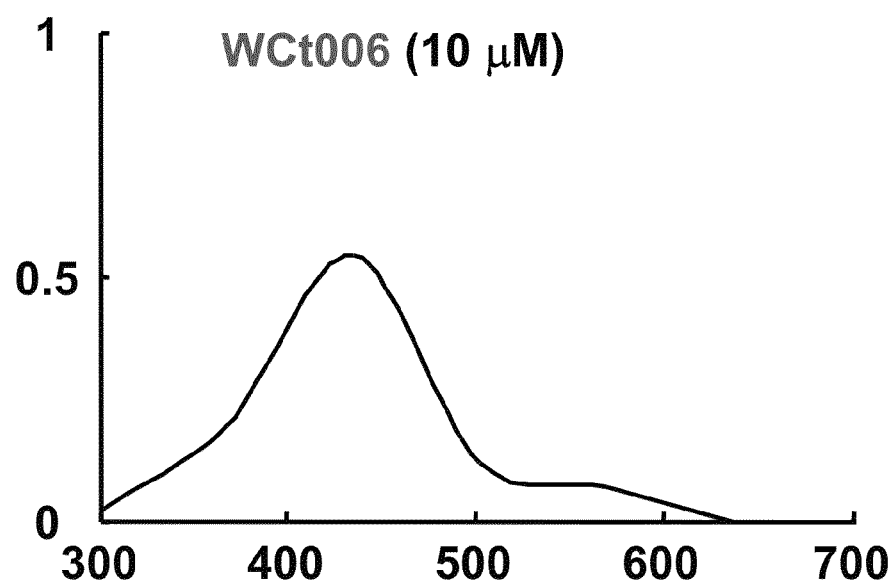
FIG. 7 shows the test results of the SOD-like activity of the six-coordinate nickel complex derivative, Ni—OH—$H_2$BDPP (WCt006), by the WST SOD assay kit. The lower drawing shows the test results of a blank control group.
Figure 7:
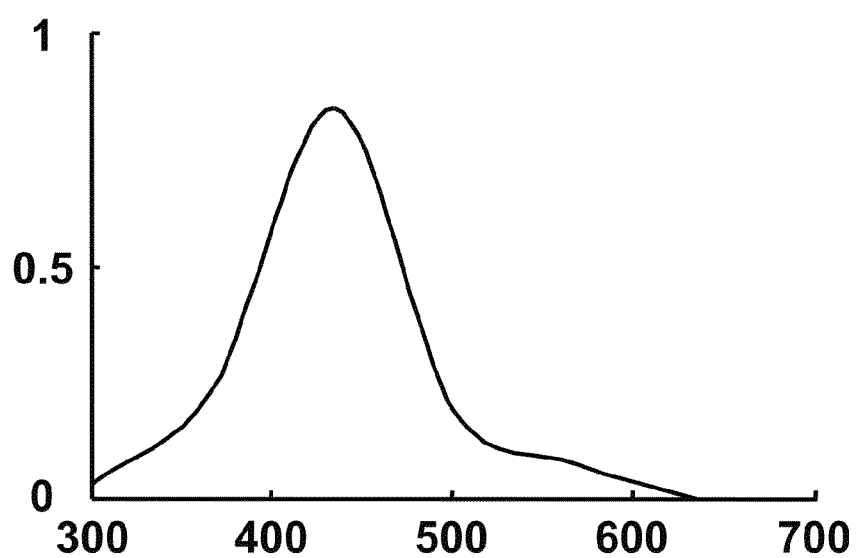

Use the WST SOD assay kit (Sigma-Aldrich) to test the SOD-like activity of the five-coordinate nickel complex, WCt005, and the six-coordinate nickel complex, WCt006. In the test, add 20 μL sample solution into the sample hole; add 20 μL ddH$_2$O into the blank control-group hole. Next, add 200 μL WST working fluid into each hole. Next, add 20 μL dilution buffer into each hole. Next, add 20 μL enzyme working fluid into the sample hole and the blank hole. Next, place the experimental group and the control group in an incubator at 37° C. for 20 minutes. Then, use a microplate reader to count at a wavelength of 450 nm, and calculate the counting results to obtain the activities, which are shown in FIG. 6 and FIG. 7, respectively.

Embodiment VI

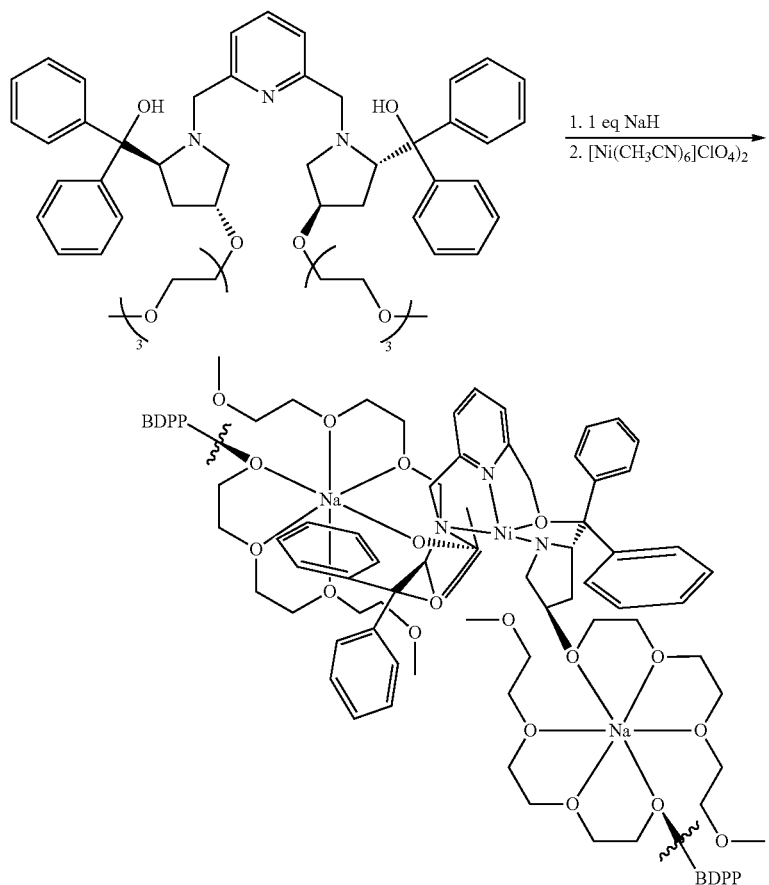

This embodiment adopts a reaction precursor OTEG-BDPP wherein the pyrrolidinyl group is replaced by $(OCH_2CH_2)_3OMe$. Similarly to Embodiment I, let 0.187 g (0.2 mmol) OTEG-BDPP sequentially react with 0.012 g (0.5 mmol) NaH and 0.101 g (0.2 mmol) $[Ni(CH_3CN)_6](ClO_4)_2$ at ambient temperature for 2 hours to obtain the derivative of the five-coordinate nickel(II) complex, Ni-OTEG-BDPP (WCt007), with a yield of 55% (0.1323 g). The characteristic peak of $[NaNi\text{-}OTEG\text{-}BDPP](ClO_4)$ is observed in ESI-MS (m/z=990.2 for $(HNi\text{-}OTEG\text{-}BDPP^+)$. The X-ray single crystal diffraction shows that Ni-OTEG-BDPP has the following structure:

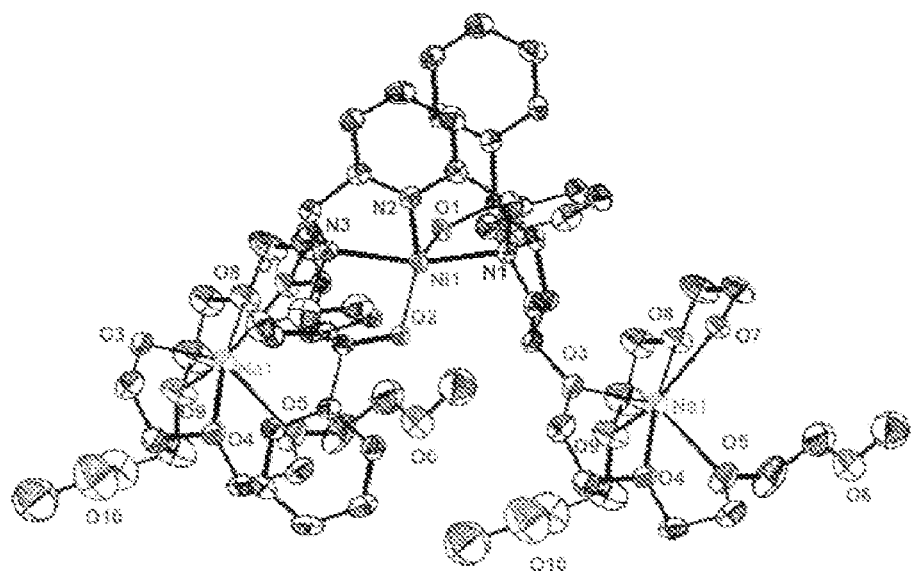

Figure 8:
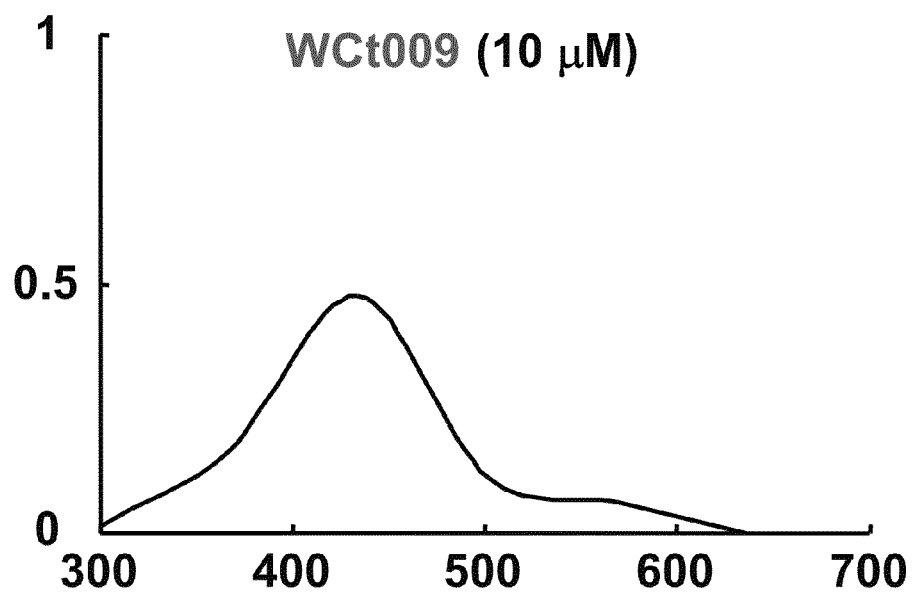
FIG. 8 shows the test results of the SOD-like activity of the six-coordinate nickel complex derivative, Ni-OTEG-$H_2$BDPP (WCt009), by the WST SOD assay kit. The lower drawing shows the test results of a blank control group.
Figure 8:
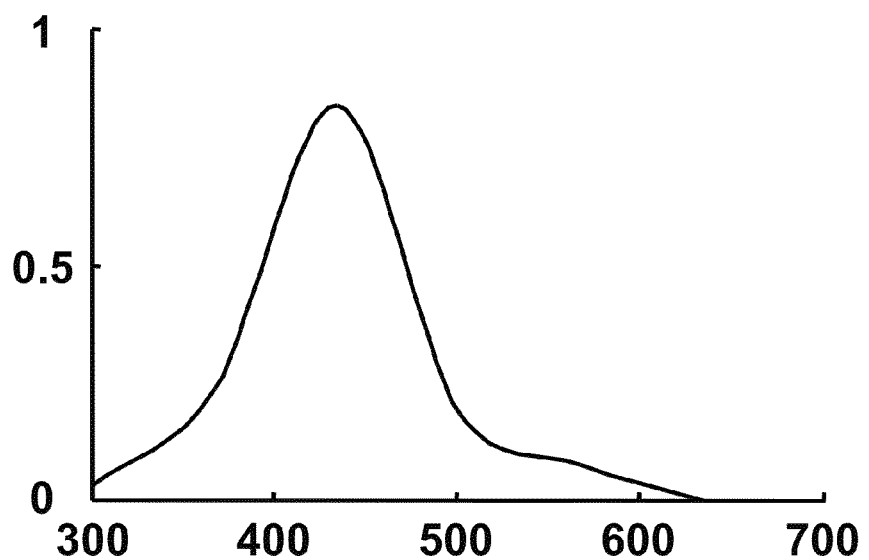

Use the WST SOD assay kit (Sigma-Aldrich) to test the SOD-like activity of the five-coordinate nickel(II) complex, WCt007. In the test, add 20 μL sample solution into the sample hole; add 20 μL ddH$_2$O into the blank control-group hole. Next, add 200 μL WST working fluid into each hole. Next, add 20 μL dilution buffer into each hole. Next, add 20 μL enzyme working fluid into the sample hole and the blank hole. Next, place the experimental group and the control group in an incubator at 37° C. for 20 minutes. Then, use a microplate reader to count at a wavelength of 450 nm, and calculate the counting results to obtain the activity, which is shown in FIG. 8.

The activity tests in the abovementioned embodiments prove that the five or six-coordinate nickel complex and their derivatives of the present invention have the activity similar to that of SOD or peroxidase.

Each of the characteristics disclosed in the specification can be replaced by an identical, equivalent or similar characteristic without departing from the spirit of the present invention. Except otherwise defined, each of the characteristics disclosed in the specification is only an exemplification of a group of identical, equivalent, and similar characteristics.

According to the specification, the persons skilled in the art should be able to modify or vary the present invention without departing from the spirit of the present invention. Therefore, any modification or variation according to the spirit of the present invention is to be also included within the scope of the present invention.

What is claimed is:

1. A nickel complex (NiBDPP) or derivatives thereof, having a structural formula (I):

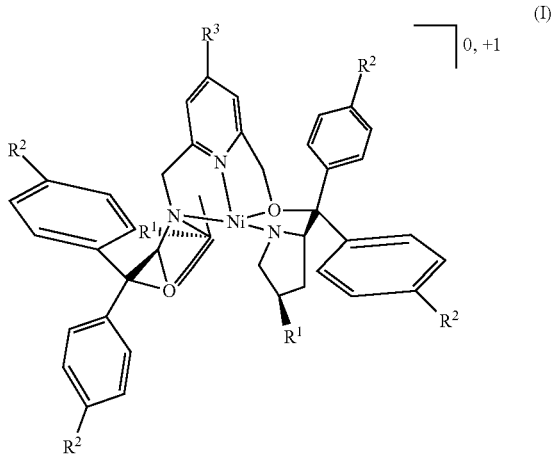

wherein R$^1$ denotes H or -A-R';
wherein A denotes O or N;
wherein R' is H, an alkoxy group, an amino acid group, or a polymeric group;
wherein said polymeric group is a polyethyleneoxy group, a polydimethylsiloxane group, or polyurethane;
wherein R$^2$ is H or a para-substituent of a phenyl ring, said para-substituent of said phenyl ring is selected from a group consisting of alkyl groups, alkoxy groups, silane groups, amino groups, alkyl amino groups, and a hydroxyl group;
wherein R$^3$ is a H or a para-substituent of a pyridine ring, said para-substituent of said pyridine ring is selected from a group consisting of amino groups, alkyl amino groups, siloxane amino groups, and siloxane amino groups which attach to a Fe$_3$O$_4$/SiO$_2$ magnetic nanoparticle; and
wherein said nickel is a nickel(II) or nickel(III) ion.

2. The nickel complex (NiBDPP) or derivatives thereof according to claim 1, wherein A is O, and R' is n pieces of ethyleneoxy group, and wherein n is an integer of from 1 to 3.

3. The nickel complex (NiBDPP) or derivatives thereof according to claim 1, wherein said para-substituent R$^2$ of said phenyl ring is a C$_{1-6}$ alkoxyl group.

4. The nickel complex (NiBDPP) or derivatives thereof according to claim 1, wherein said para-substituent R$^2$ of said phenyl ring is a C$_{1-6}$ silane group, and wherein said silane group is replaced or not replaced by a C$_{1-6}$ alkyl group.

5. A nickel complex ([NiH$_2$BDPP(L)]$^{2+}$) or derivatives thereof, which is a six-coordinate derivative having a structural formula (II):

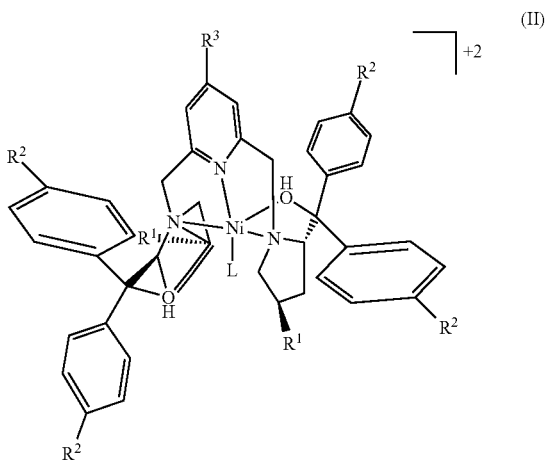

wherein R$^1$ denotes H or -A-R';
wherein A denotes O or N;
wherein R' is H an alkoxy group, an amino acid group, or a polymeric group;
wherein said polymeric group is a polyethyleneoxy group, a polydimethylsiloxane group, or polyurethane;
wherein R$^2$ is H or a para-substituent of a phenyl ring, said para-substituent of said phenyl ring is selected from a group consisting of alkyl groups, alkoxy groups, silane groups, amino groups, alkyl amino groups, and a hydroxyl group;
wherein R$^3$ is a H or a para-substituent of a pyridine ring, said para-substituent of said pyridine ring is selected from a group consisting of amino groups, alkyl amino groups, siloxane amino groups, and siloxane amino groups which attach to a Fe$_3$O$_4$/SiO$_7$ magnetic nanoparticle; and
wherein L is acetonitrile, water or tert-butyl isocyanate.

6. An antioxidant compound containing the nickel complex (NiBDPP) or the derivatives thereof, said nickel complex (NiBDPP) or derivatives thereof having a structural formula (I):

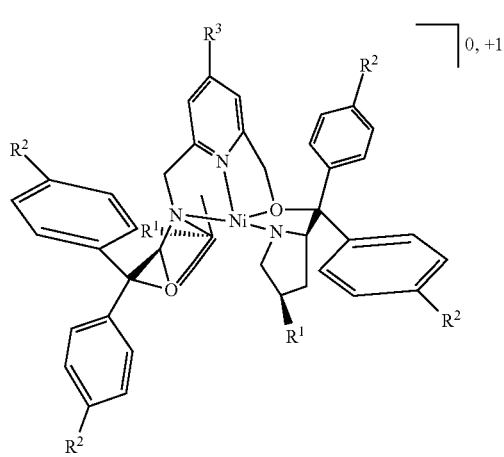 (I)

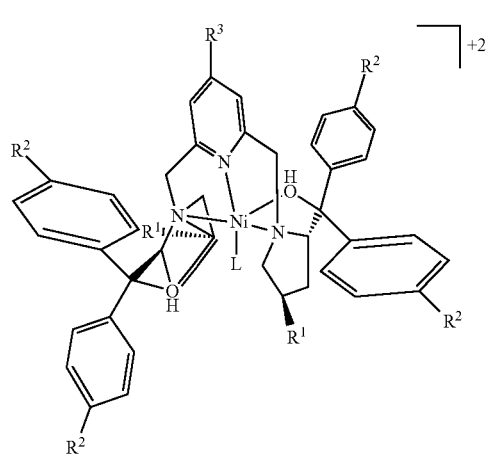 (II)

wherein $R^1$ denotes H or -A-R';
wherein A denotes O or N;
wherein R' is H, an alkoxy group, an amino acid group, or a polymeric group;
wherein said polymeric group is a polyethyleneoxy group, a polydimethylsiloxane group, or polyurethane;
wherein $R^2$ is H or a para-substituent of a phenyl ring, said para-substituent of said phenyl ring is selected from a group consisting of alkyl groups, alkoxy groups, silane groups, amino groups, alkyl amino groups, and a hydroxyl group;
wherein $R^3$ is a H or a para-substituent of a pyridine ring, said para-substituent of said pyridine ring is selected from a group consisting of amino groups, alkyl amino groups, siloxane amino groups, and siloxane amino groups which attach to a $Fe_3O_4/SiO_2$ magnetic nanoparticle; and
wherein said nickel is a nickel(II) or nickel(III) ion.

7. An antioxidant compound containing the nickel complex ($[NiH_2BDPP(L)]^{2+}$) or the derivatives thereof which is a six-coordinate derivative having a structural formula (II):

wherein $R^1$ denotes H or -A-R';
wherein A denotes O or N;
wherein R' is H, an alkoxy group, an amino acid group, or a polymeric group;
wherein said polymeric group is a polyethyleneoxy group, a polydimethylsiloxane group, or polyurethane;
wherein $R^2$ is H or a para-substituent of a phenyl ring, said para-substituent of said phenyl ring is selected from a group consisting of alkyl groups, alkoxy groups, silane groups, amino groups, alkyl amino groups, and a hydroxyl group;
wherein $R^3$ is a H or a para-substituent of a pyridine ring, said para-substituent of said pyridine ring is selected from a group consisting of amino groups, alkyl amino groups, siloxane amino groups, and siloxane amino groups which attach to a $Fe_3O_4/SiO_2$ magnetic nanoparticle; and
wherein L is acetonitrile, water or tert-butyl isocyanate.

* * * * *